United States Patent
Frąckowiak et al.

(10) Patent No.: US 9,249,167 B1
(45) Date of Patent: Feb. 2, 2016

(54) MONOVINYLGERMASILSESQUIOXANES

(71) Applicant: ADAM MICKIEWICZ UNIVERSITY, Poznań (PL)

(72) Inventors: Dawid Frąckowiak, Poznań (PL); Patrycja Żak, Poznań (PL); Bogdan Marciniec, Swarzędz (PL)

(73) Assignee: ADAM MICKIEWICZ UNIVERSITY, Poznañ (PL)

( * ) Notice: Subject to any disclaimer, the term of this patent is extended or adjusted under 35 U.S.C. 154(b) by 0 days.

(21) Appl. No.: 14/677,125

(22) Filed: Apr. 2, 2015

(30) Foreign Application Priority Data

Dec. 31, 2014 (PL) .......................................... 410690

(51) Int. Cl.
  *C07F 7/30* (2006.01)
(52) U.S. Cl.
  CPC ........................ *C07F 7/30* (2013.01)
(58) Field of Classification Search
  USPC ............................. 556/10, 434, 443, 460, 467
  See application file for complete search history.

(56) References Cited

PUBLICATIONS

Marciniec; Organometallics; 2015, 34, 3950-3958; published on Aug. 3, 2015.*

Feher et al., "Silsesquioxanes as Models for Silica Surfaces," J. Am. Chem. Soc., 1989, vol. 111, No. 5, pp. 1741-1748.
Zak et al., "Highly Effective Synthesis of Vinylfunctionalised Cubic Silsesquioxanes," Journal of Organometallic Chemistry, 2011, vol. 696, pp. 887-891.

* cited by examiner

*Primary Examiner* — Sudhakar Katakam
*Assistant Examiner* — Pancham Bakshi
(74) *Attorney, Agent, or Firm* — Oliff PLC

(57) ABSTRACT

A new cage monovinylgermasilsesquioxanes of the general formula 1,

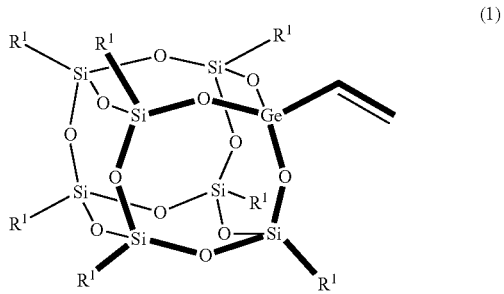

(1)

in which $R^1$ are the same and represent a $C_1$ to $C_6$ alkyl group or a cyclopentyl or cyclohexyl group or a phenyl group. The invention also relates to the method of synthesis of cage monovinylgermasilsesquioxanes of the general formula 1.

6 Claims, No Drawings

MONOVINYLGERMASILSESQUIOXANES

The invention relates to monovinylgermasilsesquioxanes and the method of their synthesis.

Monovinylgermasilsesquioxanes can be classified into the group of so-called heterosilsesquioxanes, i.e. silsesquioxanes which in addition to silicon atoms also contain other heteroatoms in their skeleton. To date, there was only one known compound containing a germanium atom in its silsesquioxane skeleton. Therefore, the germanium atom is substituted with an organic group, namely a methyl group, and there are seven cyclohexyl groups at the silicon atoms. The compound has been synthesized by Feher et al., and is characterized only on the basis of $^1$H and $^{13}$C NMR spectra (F. J. Feher, D. A. Newman, J. F. Walzer *J. Am. Chem. Soc.* 1989, 111 (5), 1741-1748).

Silsesquioxanes containing vinyl groups have an application as substrates for the synthesis of functionalized unsaturated macromolecular compounds which can contain as substituents π-conjugated olefins as well as groups containing silicon and other metalloids. The compounds are used as photophysically active components in composite materials for applications in optoelectronics or, alternatively, they can perform the function of nanofillers with diverse properties. An appropriate selection of substituents makes it possible to selectively modify the POSS over a broad range of their properties including solubility (in solvents and composite materials), photoactivity, possibility of combining with a polymer or a composite via chemical bonds in cross-linking reactions, etc.

The purpose of the invention was to synthesize a silsesquioxane molecule containing an atom of germanium and a vinyl group in the silsesquioxane skeleton.

The invention relates to new cage monovinylgermasilsesquioxanes of the general formula 1,

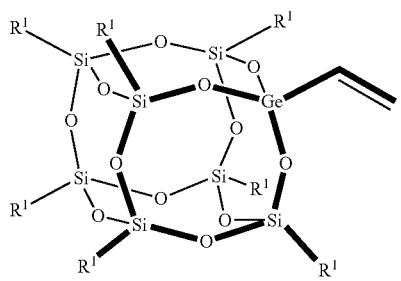
(1)

in which $R^1$ are the same and represent:
a $C_1$ to $C_6$ alkyl group
or
a cyclopentyl or cyclohexyl group
or
a phenyl group In the second aspect, the invention relates to the method of synthesis of cage monovinylgermasilsesquioxanes of the general formula 1,

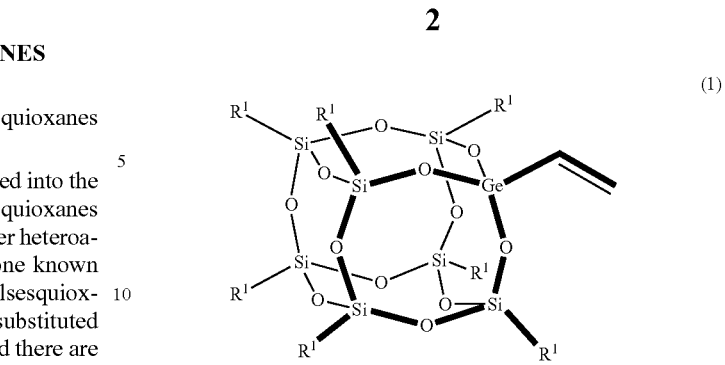
(1)

in which $R^1$ are the same and represent:
a $C_1$ to $C_6$ alkyl group
or
a cyclopentyl or cyclohexyl group
or
a phenyl group,
the method comprising the reaction between incompletely condensed trisilanols (hereinafter referred to as trisilanols POSS) of the general formula 2,

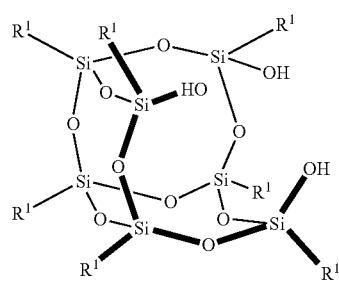
(2)

in which $R^1$ have the meaning defined above,
and vinyltrichlorogermane of the formula 3,

(3)

in the presence of an amine and a compound binding hydrogen chloride released during the reaction.

The reactions are carried out in an organic solvent selected from the group consisting of ethers, saturated hydrocarbons and aromatic hydrocarbons. It is advantageous to use solvents selected from the group consisting of THF, hexane, pentane, diethyl ether and benzene.

Due to the properties of vinyltrichlorogermane, the reaction of synthesis of vinylgermasilsesquioxanes should preferably be carried out in anhydrous conditions. Conducting the reaction in the presence of water leads to a major decrease in the yield of the process due to the high reactivity of vinyltrichlorogermane in reaction with water, producing not clearly identified germoxanes.

The reaction can be carried out in an air atmosphere, however in order to achieve the highest reaction yields, the reaction should preferably be carried out in an atmosphere of an inert gas, e.g. argon or nitrogen.

The reagents and solvents should be dried so as to avoid the formation of by-products which can be very difficult or even impossible to separate from the product proper.

The reaction can be carried out over a broad temperature range, however it is advantageously carried out at room temperature, since higher temperatures do not have a significant effect on increasing the yield, whereas reducing the temperature has a substantial effect on decreasing the yield of the reaction.

The amine can be selected from trialkyl- or dialkylamines, and it is particularly advantageous to use triethylamine. The amine plays the role of a reagent initiating the reaction between trisilanol POSS and vinyltrichlorogermane. At the same time, the amine can perform the function of a compound binding hydrogen chloride which is a product of the condensation reaction.

The agent binding hydrogen chloride can be any compound dissolving in the reaction environment and forming a stable salt with chloride anions.

The synthesis reaction takes place at the molar ratio of the reagents [vinyltrichlorogermane]:[trisilanol POSS] of 1:1. It is advantageous to use a slight excess of vinyltrichlorogermane. The reaction involves the use of an amine in an amount not less than one equivalent relative to trisilanol POSS, however when the amine is also used as an agent binding hydrogen chloride, it is used in an amount not less than 3.6 equivalents relative to vinyltrichlorogermane.

It is advantageous to carry out the reaction by applying the following sequence of adding reagents: first, dissolve trisilanol POSS in a selected solvent, then add an amine and mix the entire contents intensively for several minutes, and afterwards add vinyltrichlorogermane, advantageously in small portions. A change in the sequence of adding reagents may result in reduced reaction yield or the formation of a large quantity of by-products, e.g. as a result of incomplete condensation of the germasilsesquioxane cage or side reactions related to the ineffective binding of released hydrogen chloride which can initiate self-condensation or significant structural changes in trisilanol POSS.

The products are purified in the following manner:
  a) if the reaction is carried out in saturated hydrocarbons (e.g. pentane, hexane) or aromatic hydrocarbons (e.g. benzene, toluene), upon its completion the formed ammonium salt is filtered off, and the solvent is evaporated under reduced pressure. The dry residue is combined with a solution of methanol in water, advantageously at a concentration between 75 and 80%, in order to wash away soluble residues of substrates and by-products. The products, which have the form of powders, are filtered off and finally dried under reduced pressure. Depending on its intended application, the product is purified further using known methods.
  b) if the reaction is carried out in ethers, the solvent should be evaporated under reduced pressure and then the residue should be combined with a small amount of a light saturated hydrocarbon (e.g. pentane, hexane or petroleum ether), in which the reaction product is dissolved for the purpose of separation from residues of the ammonium salt whose solubility in ether solvents is slightly higher than in hydrocarbons. The ammonium salt precipitate is then filtered off, and the solvent is removed from the filtrate under reduced pressure. The dry residue is combined with a solution of methanol in water, advantageously at a concentration between 75 and 80%, in order to wash away soluble residues of substrates and by-products. The products, which have the form of powders, are filtered off and finally dried under reduced pressure. Depending on its intended application, the product is purified further using known methods.

Known cubic vinylsubstituted silsesquioxanes are compounds used as precursors for functionalized unsaturated POSS containing π-conjugated olefins as substituents; such compounds have an application as well-defined stable chromophores and photoactive nanofillers (B. Marciniec, P. Żak, M. Majchrzak, C. Pietraszuk, *J. Organomet. Chem.*, 2011, 696, 887). Due to the presence of a Ge—O—Si group in their structure germasiloxanes are characterized by higher values of the refractive index than siloxanes, which is why oligo- and polymeric germasiloxanes are applied in the manufacture of specialized spin glasses, glass films, microlenses, lasers and adhesive layers.

The compounds according to the invention contain Ge—O—Si bonds in their structure, and hence combine the characteristics of known silsesquioxanes with properties of compounds containing a Ge—O—Si group, which makes them suitable for application in composite optical materials or a substrate in the synthesis of functionalized oligomers with specific electron properties determined both by substituents bound to the germasilsesquioxane core and through the Ge—O—Si bond itself.

The introduction of a germanium atom into the POSS cage structure produces compounds exhibiting similar characteristics as POSS containing only silicon and, at the same time, due to the introduction of a germanium atom into the silsesquioxane cage and different properties and reactivity of the vinyl group at the germanium atom, makes it possible to synthesize compounds of diverse properties, having the characteristics of nanofillers and compounds with specific optical properties, which can have an application for the manufacture of optical materials with specific parameters.

The method according to the invention is presented in examples given below which do not limit the applications of the invention.

Identification data of acquired compounds are listed in a table.

The analysis of products was performed with:
  the $^1$H and $^{13}$C-NMR spectra were recorded on a Varian Gemini 300 spectrometer at 300 and 75 MHz,
  the $^{29}$Si NMR spectra were recorded on a Varian Avance 600 spectrometer at 119.203 MHz,
  the mass spectra were recorded on a 4000 Q TRAP system from Applied Biosystems.

EXAMPLE I

A two-necked flask with a volume of 500 mL, equipped with a reflux condenser and an adapter for introducing inert gas, was loaded in an argon atmosphere with trisilanolisobutyl POSS (5 g, 6.32 mmol), deoxygenated and dried tetrahydrofuran (200 mL), and triethylamine (3.17 mL, 22.75 mmol). Next, vinyltrichlorogermane (0.95 mL, 7.58 mmol) was added drop by drop into the reaction mixture, at room temperature, resulting in the formation of white precipitate of ammonia salt. The suspension was mixed for 24 h at room temperature, and then filtered in air on a glass sinter connected to a membrane pump. The precipitate was washed with tetrahydrofuran (3×10 mL), and the resulting filtrate was evaporated until dryness. The residues were then combined with a cold aqueous solution of methanol, which led to the formation of white precipitate that was filtered on a glass sinter funnel. Monovinylheptaisobutylgermasilsesquioxane in the form of white powder was obtained with a yield of 89%.

EXAMPLE II

Following the procedure set out in Example I, a reaction was carried out between trisilanolethyl POSS (5 g, 7.22 mmol), triethylamine (3.62 mL, 25.99 mmol) and vinyltrichlorogermane (1.08 mL, 8.66 mmol). Monovinylheptaethylgermasilsesquioxane in the form of white powder was obtained with a yield of 92%.

EXAMPLE III

Following the procedure set out in Example I, a reaction was carried out between trisilanolphenyl POSS (5 g, 4.86 mmol), triethylamine (2.44 mL, 17.51 mmol) and vinyltrichlorogermane (0.73 mL, 5.83 mmol). Monovinylheptaphenylgermasilsesquioxane in the form of white powder was obtained with a yield of 90%.

EXAMPLE IV

Following the procedure set out in Example I, a reaction was carried out between trisilanolcyclopentyl POSS (5 g, 5.14 mmol), triethylamine (2.60 mL, 18.50 mmol) and vinyltrichlorogermane (0.77 mL, 6.17 mmol). Monovinylheptacyclopentylgermasilsesquioxane in the form of white powder was obtained with a yield of 87%.

EXAMPLE V

Following the procedure set out in Example I, a reaction was carried out between trisilanolcyclohexyl POSS (5 g, 4.67 mmol), triethylamine (2.34 mL, 16.82 mmol) and trichlorovinyl-germanane (0.7 mL, 5.6 mmol). Monovinylheptacyclohexylgermasilsesquioxane in the form of white powder was obtained with a yield of 84%.

TABLE

| EXAMPLE I | |
|---|---|
| Name of chemical compound | Monovinylheptaisobutylgermasilsesquioxane |
| Formula of chemical compound | (structure of iBu-substituted germasilsesquioxane cage with vinyl group on Ge) |
| NMR analysis + HRMS analysis | $^1$H NMR (CDCl$_3$, δ, ppm): 0.58-0.64 (m, 14H, CH$_2$), 0.92-0.97 (m, 42H, CH$_3$), 1.80-1.91 (m, 7H, CH), 6.01 (dd, 1H, J$_{HH}$ = 19.9, 12.6 Hz, CH=CH$_2$), 6.11 (dd, 1H, J$_{HH}$ = 19.9, 3.1 Hz, CH=CH$_2$), 6.19 (dd, 1H, J$_{HH}$ = 12.6, 3.1 Hz, CH=CH$_2$); $^{13}$C NMR (CDCl$_3$, δ, ppm): 22.60, 22.92 (CH$_2$), 23.86, 23.97 (CH), 25.68, 25.72 (CH$_3$), 126.50 (=CH—Ge), 137.12 (=CH$_2$) $^{29}$Si NMR (CDCl$_3$, δ, ppm): −65.7, −67.6, −68.15 MS (ASAP): m/z (%): 885.23 (40), 887.22 (68), 889.22 (100), 890.22 (66), 891.22 (54), 892.22 (28), 893.22 (13) HRMS (ASAP) for C$_{30}$H$_{67}$GeO$_{12}$Si$_7$: calcd 889.2229; found 1889.2236 |

| EXAMPLE II | |
|---|---|
| Name of chemical compound | Monovinylheptaethylgermasilsesquioxane |
| Formula of chemical compound | (structure of Et-substituted germasilsesquioxane cage with vinyl group on Ge) |
| NMR analysis + HRMS analysis | $^1$H NMR (CDCl$_3$, δ, ppm): 0.56-0.66 (m, 21H, CH$_3$), 0.96-1.03 (m, 14H, CH$_2$), 6.03 (dd, 1H, J$_{HH}$ = 19.9, 12.6 Hz, CH=CH$_2$), 6.14 (dd, 1H, J$_{HH}$ = 19.9, 3.1 Hz, CH=CH$_2$), 6.21 (dd, 1H, J$_{HH}$ = 12.6, 3.1 Hz, CH=CH$_2$) $^{13}$C NMR (CDCl$_3$, δ, ppm): 4.12, 4.49 (CH$_2$), 6.51, 6.73 (CH$_3$), 126.39 (=CH—Ge), 137.23 (=CH$_2$) $^{29}$Si NMR: (CDCl$_3$, δ, ppm): −63.62, −65.11, −65.68 MS (ASAP): m/z (%): 660.96 (12), 662.96 (21), 664.96 (11), 678.97 (28), 682.98 (17), 689 (31), 691 (60), 693 (100), 694 (48), 695 (39), 701.98 (13), 702.98 (11), 703.99 (22), 704.98 (13) HRMS (ASAP) for C$_{16}$H$_{39}$GeO$_{12}$Si$_7$: calcd 693.0038; found 693.0032; |

TABLE-continued

EXAMPLE III

Name of chemical compound: Monovinylheptaphenylgermasilsesquioxane

Formula of chemical compound:

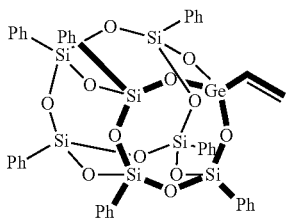

NMR analysis + HRMS analysis:
$^1$H NMR (CDCl$_3$, δ, ppm): 6.16 (dd, 1H, J$_{HH}$ = 19.8, 12.3 Hz, CH=CH$_2$), 6.25 (dd, 1H, J$_{HH}$ = 17.1, 2.7 Hz, CH=CH$_2$), 6.30 (dd, 1H, J$_{HH}$ = 9.7, 2.7 Hz, CH=CH$_2$), 7.30-7.81 (m, 35H, Ph)
$^{13}$C NMR (CDCl$_3$, δ, ppm): 127.78 (=CH—Ge), 130.44, 130.52, 130.63, 131.19 (ipso-C with C$_6$H$_5$), 134.17 (=CH$_2$)
$^{29}$Si NMR: (CDCl$_3$, δ, ppm): −76.99, −78.12, −78.58
MS (ASAP): m/z (%): 889.22 (25), 1025.01 (36), 1027.01 (62), 1029.01 (100), 1030.01 (72), 1031.01 (58), 1032.01 (30)
HRMS (ASAP) for C$_{44}$H$_{39}$GeO$_{12}$Si$_7$: calcd 1029.0038; found 1029.0056

EXAMPLE IV

Name of chemical compound: Monovinylheptacyclopentylgermasilsesquioxane

Formula of chemical compound:

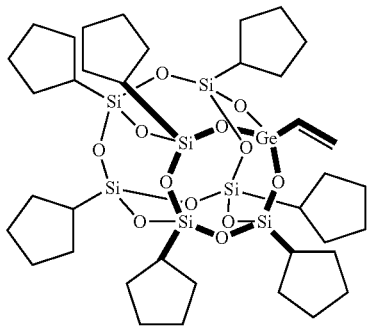

NMR analysis + HRMS analysis:
$^1$H NMR (CDCl$_3$, δ, ppm): 0.88-1.27 (m, 7H, cyclopentyl-CH), 1.36-1.90 (m, 56H, cyclopentyl-CH$_2$), 6.02 (dd, 1H, J$_{HH}$ = 19.8, 11.8 Hz, CH=CH$_2$), 6.12 (dd, 1H, J$_{HH}$ = 20.8, 5.0 Hz, CH=CH$_2$), 6.20 (dd, 1H, J$_{HH}$ = 8.4, 3.4 Hz, CH=CH$_2$)
$^{13}$C NMR (CDCl$_3$, δ, ppm): 22.34, 22.81 (cyclopentyl-CH), 26.97, 27.02, 27.30, 27.53 (cyclopentyl-CH$_2$), 126.76 (=CH—Ge), 136.89 (=CH$_2$)
$^{29}$Si NMR: (CDCl$_3$, δ, ppm): −64.26, −65.76, −66.35
MS (ASAP): m/z (%): 835.08 (49), 903.14 (17), 921.15 (100), 944.17 (76), 973.22 (80)
HRMS (ASAP) for C$_{37}$H$_{67}$GeO$_{12}$Si$_7$: calcd 973.2209; found 973.2229

EXAMPLE V

Name of chemical compound: Monovinylheptacyclohexylgermasilsesquioxane

Formula of chemical compound:

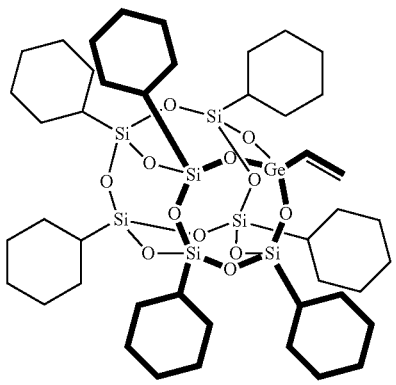

TABLE-continued

| NMR analysis + HRMS analysis | $^1$H NMR (CDCl$_3$, δ, ppm): 0.55-0.68 (m, 7H, cyclohexyl-CH), 0.99-1.19 (m, 35H, cyclohexyl-CH$_2$), 1.47-1.68 (m, 35H, cyclohexyl-CH$_2$), 5.87 (dd, 1H, $J_{HH}$ = 19.9, 12.9 Hz, CH=CH$_2$), 5.98 (dd, 1H, $J_{HH}$ = 19.9, 2.9 Hz, CH=CH$_2$), 6.06 (dd, 1H, $J_{HH}$ = 12.9, 2.8 Hz, CH=CH$_2$) $^{13}$C NMR (CDCl$_3$, δ, ppm): 21.77, 22.74 (cyclohexyl-CH), 25.19, 25.42, 25.45, 26.05, 26.10 (cyclohexyl-CH$_2$), 125.78 (=CH—Ge), 136.29 (=CH$_2$) $^{29}$Si NMR: (CDCl$_3$, δ, ppm): −68.56, −70.00, −70.52 MS (ASAP): m/z (%): 905.16 (39), 987.24 (15), 1005.25 (100), 1028.27 (72), 1071.33 (49) HRMS (ASAP) for C$_{44}$H$_{81}$GeO$_{12}$Si$_7$: calcd 1071.3319; found 1071.3325 |
|---|---|

The invention claimed is:

1. Cage monovinylgermasilsesquioxanes of the general formula 1,

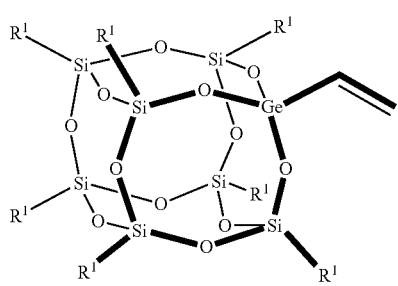

(1)

in which R$^1$ are the same and:
are selected from the group consisting of a C$_1$ to C$_6$ alkyl group, a cyclopentyl group, a cyclohexyl group and a phenyl group.

2. A method of synthesis of the cage monovinylgermasilsesquioxanes of claim 1,
the method comprising a reaction between incompletely condensed trisilanols of the general formula 2,

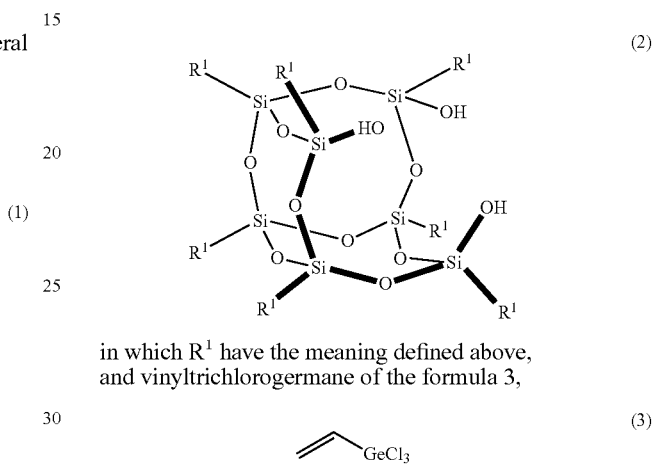

(2)

in which R$^1$ have the meaning defined above,
and vinyltrichlorogermane of the formula 3, $$\diagup\!\!\!\diagup\text{GeCl}_3 \qquad (3)$$

in the presence of an amine and a compound binding hydrogen chloride.

3. The method, as claimed in claim 2, wherein the amine can be selected from trialkyl- or dialkylamines.

4. The method, as claimed in claim 3, wherein the amine is triethylamine.

5. The method, as claimed in claim 2, wherein the amine is used in an amount not less than one equivalent relative to trisilanol.

6. The method, as claimed in claim 3, wherein the amine is used in an amount not less than one equivalent relative to trisilanol.

* * * * *